US012626473B2

(12) United States Patent
Dashwood

(10) Patent No.: US 12,626,473 B2
(45) Date of Patent: May 12, 2026

(54) DYNAMIC VIRTUAL OBJECTS

(71) Applicant: Apple Inc., Cupertino, CA (US)

(72) Inventor: Jack R. Dashwood, Santa Clara, CA (US)

(73) Assignee: Apple Inc., Cupertino, CA (US)

( * ) Notice: Subject to any disclaimer, the term of this patent is extended or adjusted under 35 U.S.C. 154(b) by 127 days.

(21) Appl. No.: 18/769,972

(22) Filed: Jul. 11, 2024

(65) Prior Publication Data

US 2025/0078433 A1     Mar. 6, 2025

Related U.S. Application Data

(60) Provisional application No. 63/536,584, filed on Sep. 5, 2023.

(51) Int. Cl.
G06T 19/20 (2011.01)
A61B 5/00 (2006.01)

(52) U.S. Cl.
CPC ............ G06T 19/20 (2013.01); A61B 5/4519 (2013.01); *G06T 2219/2004* (2013.01); *G06T 2219/2016* (2013.01)

(58) Field of Classification Search
CPC ...................... G06T 19/20; G06T 2219/2004
See application file for complete search history.

(56) References Cited

U.S. PATENT DOCUMENTS

| | | | |
|---|---|---|---|
| 7,239,718 | B2 | 7/2007 | Park et al. |
| 8,213,680 | B2 | 7/2012 | Fitzgibbon et al. |
| 9,746,671 | B2 | 8/2017 | Fujigaki |
| 9,824,698 | B2 | 11/2017 | Jerauld |
| 9,851,374 | B2 | 12/2017 | Clark et al. |
| 10,073,541 | B1 | 9/2018 | Baldwin |
| 10,463,958 | B2 | 11/2019 | Bentley |
| 11,544,865 | B1 | 1/2023 | Kurz |
| 2011/0270135 | A1 | 11/2011 | Dooley et al. |
| 2011/0275045 | A1 | 11/2011 | Bhupathi |

(Continued)

FOREIGN PATENT DOCUMENTS

| | | |
|---|---|---|
| EP | 3422296 | 1/2019 |
| WO | 2014145711 A1 | 9/2014 |
| WO | 2019183733 A1 | 10/2019 |

OTHER PUBLICATIONS

Baptista, R. et al., "Video-Based Feedback for Assisting Physical Activity," 12th International Joint Conference on Computer Vision, Imaging and Computer Graphics Theory and Applications (VISAPP), 7 pages, 2017.

(Continued)

*Primary Examiner* — Matthew Salvucci
(74) *Attorney, Agent, or Firm* — Thompson Hine LLP

(57) ABSTRACT

Some implementations offset or reduce user fatigue and/or discomfort by making relatively small (e.g., potentially imperceptible) changes to relative positions of virtual objects (e.g., virtual screens) or entire scenes to cause or encourage the user to make small adjustments, e.g., changing their posture. By periodically making small changes over long periods of time, the changes may be imperceptible, inspire unconscious user posture changes or movements, and/or improve the user experience without burdening or distracting the user from their desired activity, e.g., watching a movie, working on a virtual UI interface, etc.

24 Claims, 5 Drawing Sheets

(56) References Cited

U.S. PATENT DOCUMENTS

| | | | |
|---|---|---|---|
| 2012/0116257 | A1 | 5/2012 | Leuthardt |
| 2012/0268364 | A1 | 10/2012 | Minnen |
| 2015/0309579 | A1 | 10/2015 | Wang |
| 2016/0027325 | A1 | 1/2016 | Malhotra |
| 2017/0206691 | A1 | 7/2017 | Harrises et al. |
| 2017/0231490 | A1 | 8/2017 | Toth et al. |
| 2017/0358241 | A1 | 12/2017 | Wexler |
| 2018/0249150 | A1 | 8/2018 | Takeda et al. |
| 2019/0077007 | A1 | 3/2019 | Mallinson |
| 2019/0139312 | A1 | 5/2019 | Leppänen |
| 2019/0224528 | A1 | 7/2019 | Omid-Zohoor |
| 2021/0154529 | A1 | 5/2021 | Barr |
| 2021/0268361 | A1 | 9/2021 | Putnam |
| 2022/0351824 | A1 | 11/2022 | Weissberger |
| 2024/0386643 | A1* | 11/2024 | Hoover .............. G02B 27/0081 |
| 2025/0148623 | A1 | 5/2025 | Mondal |

OTHER PUBLICATIONS

Lee, S. and Lee, S.H., "Projective Motion Correction with Contact Organization," IEEE Transactions on Visualization and Computer Graphics, vol. 25, No. 4, 14 pages, 2019.

Gupta, A. et al., "Diagonal State Spaces are as Effective as Structured State Spaces," 2022.

Gu, A. et al., Efficiently Modeling Long Sequences with Structured State Spaces, 32 pages, 2022.

Gu, A. et al., "HIPPO: Recurrent Memory with Optimal Polynomial Projections", 47 pages, 2020.

Mehta, H. et al., "Long Range Language Modeling via Gated State Spaces", 15 pages, 2022.

Gu, A. et al., "On the Parameterization and Initialization of Diagonal State Space Models", 23 pages, 2022.

Katzakis, Nicholas, Tong, Jonathan, Ariza, Oscar, Chen, Lihan, Klinker, Gudrun, Roder, Brigitte and Steinicke, Frank, "Stylo and Handifact: Modulating Haptic Perception through Visualizations for Posture Training in Augmented Reality", SUI' 17, Oct. 16-17, 2017, Brighton, United Kingdom, pp. 1-11 2017.

4D Motion, How it Works,; https://4dmotionsports.com/how-it-works/; pp. 2-8; Jan. 28, 2021 2021.

Risley, James; "Why this startup is looking at Al to make your golf swing better"; pp. 1-6, Nov. 8, 2016. 2016.

Swingbyte; "Say Hello to the Swingbyte Virtual Coach", pp. 1-4, Jan. 28, 2021. 2021.

Golf Swing Analysis App; Lukas Kidzinski; pp. 1-2; 2017. 2017.

FitV Home; "Get Feedback. See Results.", pp. 1-3; 2021. 2021.

Nie, Q., Wang, J., Wang, X., & Liu, Y. (2019). View-invariant human action recognition based on a 3D bio-constrained skeleton model. IEEE Transactions on Image Processing, 28(8), 3959-3972. (Year: 2019) 2019.

Li, Zongmian et al., "Estimating 3d motion and forces of person-object interactions from monocular video," Proceedings of the IEEE/CVF Conference on Computer Vision and Pattern Recognition, 2019.

* cited by examiner

700

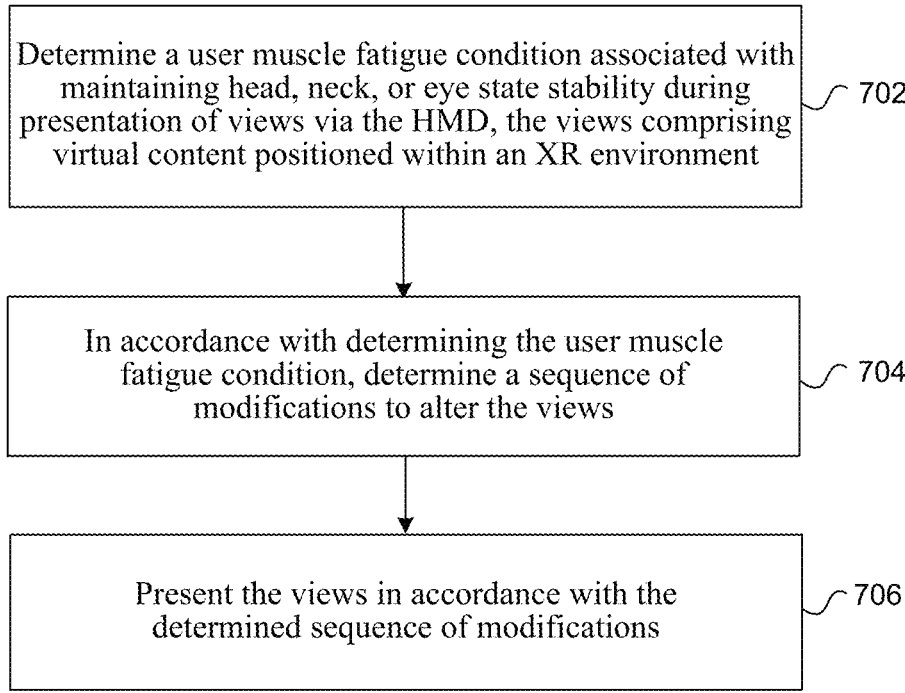

Determine a user muscle fatigue condition associated with maintaining head, neck, or eye state stability during presentation of views via the HMD, the views comprising virtual content positioned within an XR environment  ⌐ 702

In accordance with determining the user muscle fatigue condition, determine a sequence of modifications to alter the views  ⌐ 704

Present the views in accordance with the determined sequence of modifications  ⌐ 706

FIG. 7

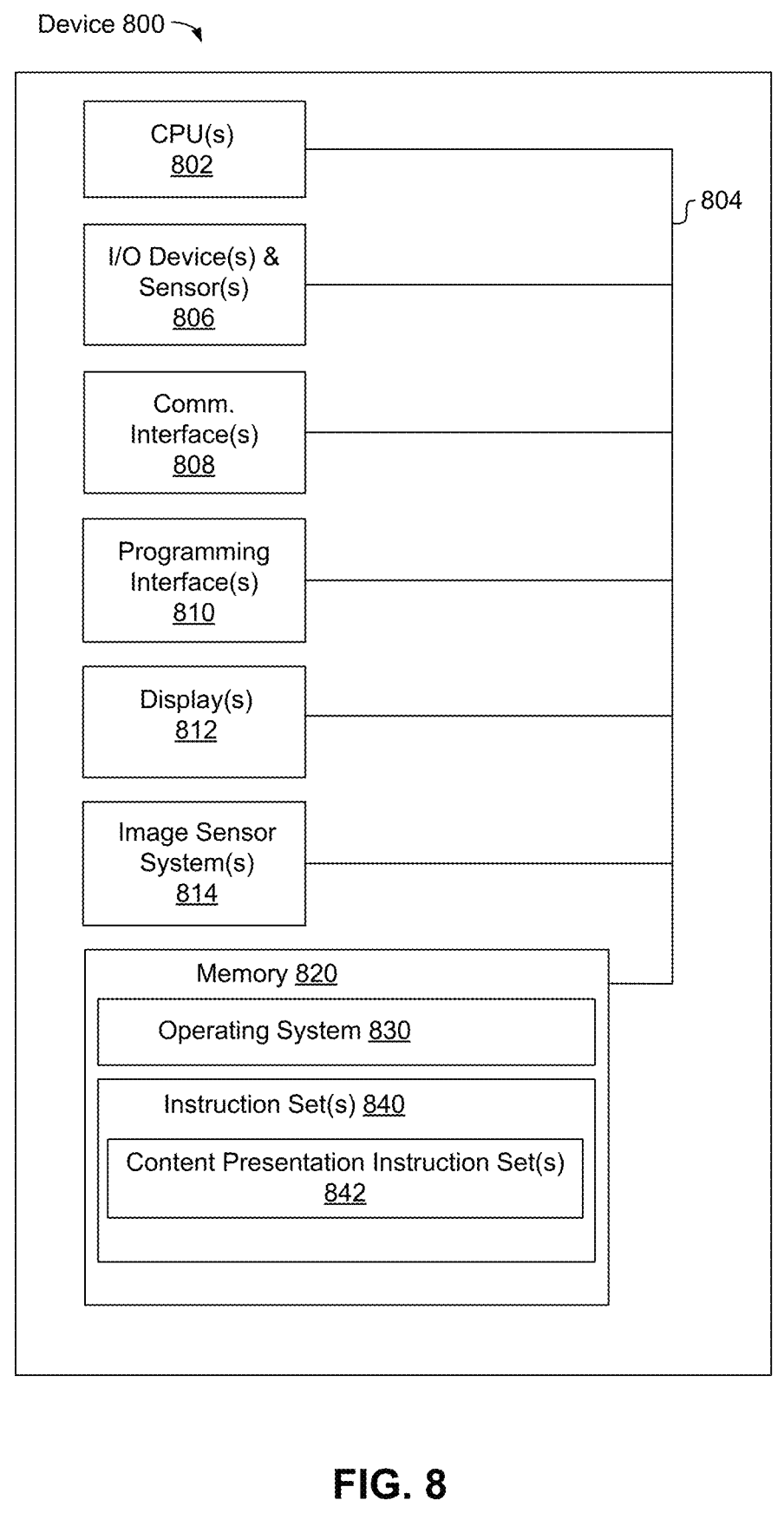

Device 800

CPU(s)
802

I/O Device(s) &
Sensor(s)
806

Comm.
Interface(s)
808

Programming
Interface(s)
810

Display(s)
812

Image Sensor
System(s)
814

804

Memory 820

Operating System 830

Instruction Set(s) 840

Content Presentation Instruction Set(s)
842

FIG. 8

DYNAMIC VIRTUAL OBJECTS

CROSS-REFERENCE TO RELATED APPLICATIONS

This Application claims the benefit of U.S. Provisional Application Ser. No. 63/536,584 filed Sep. 5, 2023, which is incorporated herein in its entirety.

TECHNICAL FIELD

The present disclosure generally relates to electronic devices, and in particular, to systems, methods, and devices for reducing user fatigue and/or discomfort during use of electronic devices.

BACKGROUND

Users of electronic devices (e.g., head mounted devices (HMDs), wearable electronic devices, desktop computers, laptops, mobile devices, televisions, and other electronic devices) sometimes experience fatigue and associated discomfort when using those devices for relatively long periods of time. For example, a user holding their head, neck, and/or torso in a generally static position to view a movie on a virtual screen positioned within an extended reality (XR) environment may experience fatigue and associated discomfort over the course of the movie.

SUMMARY

As discussed above, users of electronic devices sometimes experience fatigue when using those devices for long periods of time during which there may be little or no head, neck, eye, torso, or other body movements. Some implementations offset or reduce user fatigue or the associated discomfort by making relatively small (e.g., potentially imperceptible) changes to relative positions of virtual objects (e.g., virtual screens) or entire scenes to cause or encourage the user to make small adjustments, e.g., changing their posture or moving their bodies over time. By periodically making small changes over long periods of time, the changes may be imperceptible, inspire unconscious user posture changes or movements, and/or improve the user experience without burdening or distracting the user from their desired activity, e.g., watching a movie, working on a virtual UI interface, etc.

Some implementations identify a user fatigue condition associated with maintaining head, neck, or eye state stability during presentation of content in XR. Doing so may involve subtly changing the content over time (e.g., changing the height of the virtual screen or focal distance used to display the XR) in an imperceptible way to encourage the user to alter muscle usage to reduce the fatigue that might otherwise develop from holding the head, neck, or eyes in a stable/fixed state.

Various implementations disclosed herein include devices, systems, and methods for reducing user fatigue and the associated discomfort during use of an electronic device. Such methods may determine a user muscle fatigue condition associated with maintaining head, neck, or eye state stability during presentation of views via the HMD. The views may comprise virtual content positioned within an extended reality (XR) environment. Determining the user muscle fatigue condition may involve determining that the user's head, eyes, and/or neck (or other body portions) have remained stable or are expected to continue in a stable state based on sensor data regarding the user or information about the content, e.g., the type of content being a movie, etc. In accordance with determining the user muscle fatigue condition, the methods may determine a sequence of modifications to alter the views. The sequence of modification may comprise: view-to-view modifications that change a parameter less than a first threshold amount between consecutive views during the presentation of the views; (e.g., changes small enough from frame to frame so that they are not consciously perceptible/objectionable). The sequence of modification may comprise: a cumulative modification of the parameter over the sequence of modifications that changes the parameter more than a second threshold amount (e.g., the changes being cumulatively significant enough to encourage the user to alter muscle usage to reduce fatigue and associated discomfort that might otherwise develop. The methods may present the views in accordance with the determined sequence of modifications.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIG. 7 is a flowchart illustrating an exemplary method of reducing user fatigue and/or discomfort during use of an electronic device, according to some implementations.

FIG. 8 illustrates an exemplary computing device in accordance with some implementations.

Figure 1:
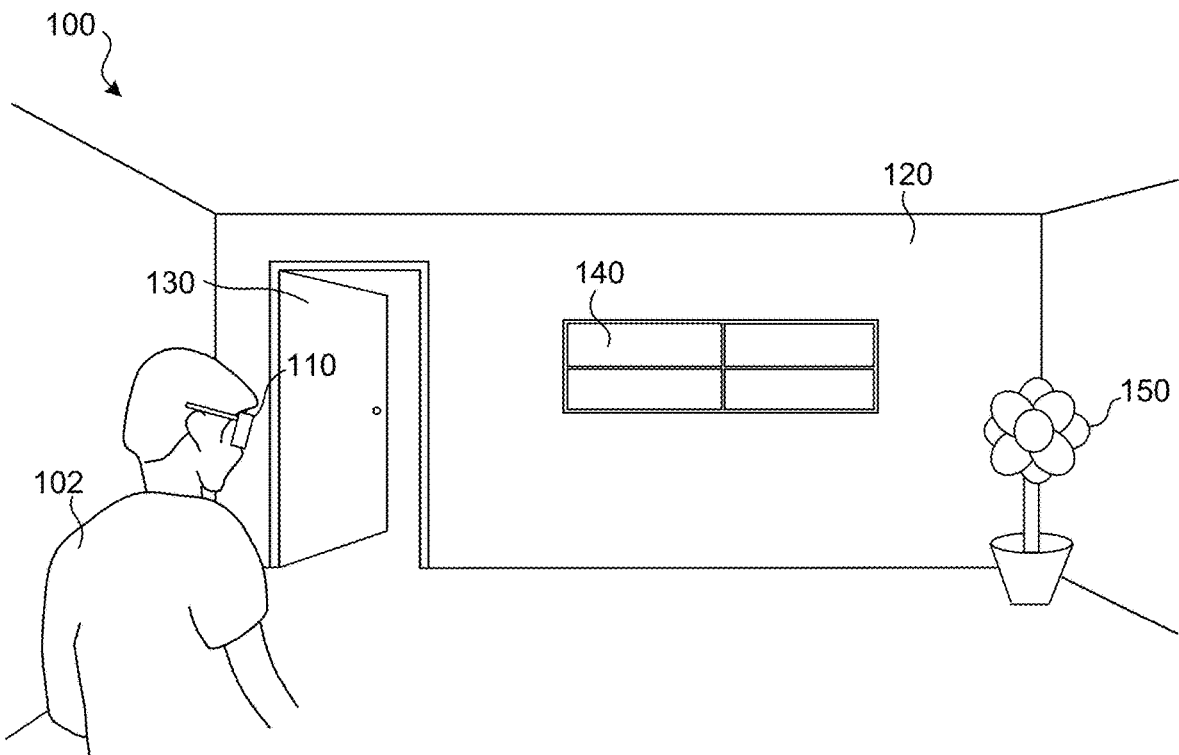
FIG. 1 illustrates an example operating environment in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein. While FIG. 1 depicts exemplary implementations involving a head mounted device (HMD), other implementations do not necessarily involve an HMD and may involve other types of devices including, but not limited to, watches and other wearable electronic devices, mobile devices, laptops, desktops, gaming devices, home automation devices, and other types of user devices.

FIG. 1 is a block diagram of an example physical environment 100 in which a device, such as device 110, may provide views in accordance with some implementations. In this example, physical environment 100 includes walls (such as wall 120), a door 130, a window 140, and a plant 150.

The electronic device 110 may include one or more cameras, microphones, depth sensors, or other sensors that can be used to capture information about and evaluate the physical environments 100 and the objects therein, as well as information about the user 102. The device 110 may use information about its physical environment 100 or user 102 that it obtains from its sensors to provide visual and audio content.

In some implementations, the device 110 is configured to present views that it generates to the user 102, including views that may be based on the physical environment 100 and one or more virtual content items. According to some implementations, the electronic device 110 generates and presents views of an extended reality (XR) environment.

In some implementations, the device 110 is a handheld electronic device (e.g., a smartphone or a tablet). In some implementations, the user 102 wears the device 110 on his/her head. As such, the device 110 may include one or more displays provided to display content. For example, the device 110 may enclose the field-of-view of the user 102.

In some implementations, the functionalities of device 110 are provided by more than one device. In some implementations, the device 110 communicates with a separate controller or server to manage and coordinate an experience for the user. Such a controller or server may be local or remote relative to the physical environment 100.

The device 110 displays content to the user 102 and adjusts the display of that content over time to inspire or encourage user changes in posture or other movements that may reduce user fatigue and associated discomfort. In some implementations, the device 110 displays virtual content using one or more parameters that are varied over time to inspire or encourage such changes or movements. In some implementations, virtual content can be displayed at gradually changing locations, heights, sizes, or shapes. These parameters of one or more virtual content item may be determined and/or varied over time. For example, one or more of the size of the video content item (e.g., its virtual screen size), the position within the environment (e.g., within the 3D space of an XR environment), the position relative to the viewer (e.g., within the 3D space of an XR environment), the height, the angle, the brightness, the color format/attributes, the display frame rate, etc. can be determined or changed over time to reduce user fatigue and associated discomfort, and/or otherwise provide a more desirable user experience. In some implementations, the display of the surrounding 3D environment is alternatively, or additionally, adjusted to reduce user fatigue, reduce discomfort, and/or otherwise provide a desirable user experience.

In some implementations, the position of a video content item, e.g., on a virtual screen or the position of a virtual screen itself, is determined. For example, a 3D movie may be presented at a position relative to the user that is determined to provide a comfortable or desirable experience. Such a position may depend upon the individual user, e.g., the user's vision quality, inter-pupillary distance (IPD), physiological attributes, or viewing preferences, which may individually or collectively provide contextual attributes used to position the video content item relative to the viewer. The position of the video content item may additionally or alternatively account for the resolution of the content or the resolution of the display, e.g., avoiding positions that will provide a pixelated appearance given the resolution of the content or display. Thus, for example, 4K content may be displayed larger than high-definition (HD) content. In some implementations, the position of the content is selected to occupy as large a portion of the displayed view (e.g., within an HMD's view) as possible while satisfying user comfort requirements, e.g., not so close that it is uncomfortable to the user. Subjective comfort may be estimated based on average/typical user physiology and preferences or based on user-specific physiology and preferences.

After an initial position for virtual content is determined and/or used to display the virtual content, that position may then be varied over time to reduce user fatigue, reduce associated discomfort, and/or otherwise provide a desirable continuing user experience.

Figure 2:
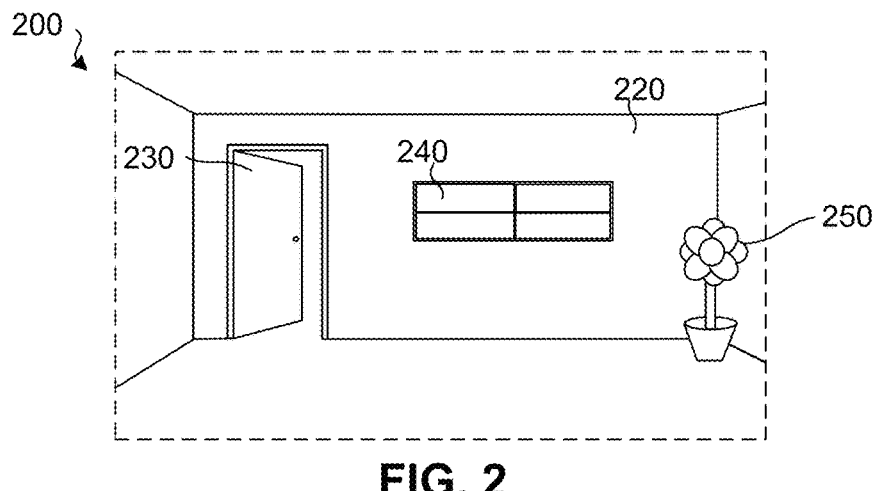
FIG. 2 illustrates a view of the environment of FIG. 1 provided by an electronic device in accordance with some implementations.

FIG. 2 is a view 200 depicting the physical environment 100 provided by the device 110 of FIG. 1. In this example, the view 200 is a view of an XR environment that depicts and enables user interactions with real or virtual objects. Such a view may include optical see through or pass-through video providing depictions of portions of the physical environment 100. In one example, one or more outward facing cameras on device 110 capture images of the physical environment that are passed through to provide at least some of the content depicted in the view 200. In this example, the view 200 includes depictions of the walls, such as depiction 220 of wall 120, depictions of the floor and ceiling, a depiction 230 of the door 130, a depiction 240 of the window 140, and a depiction 250 of the flower 150.

Some implementations subtly change aspects of an XR environment over time to reduce user fatigue, reduce discomfort, and/or otherwise provide a desirable continuing user experience. This may, for example, involve subtly changing content so that a user will make small changes to head tilt or other body positioning. Such changes, e.g., over a relatively long period of time, may vary or reduce the amount of tension in the user's muscles and thus reduce fatigue or alleviate associated discomfort. Changes may be made so that the user changes eye characteristics, e.g., inspiring or encouraging the user to change vergence/accommodation based on changes to the content or how the content is displayed by the device.

In one example, a user is watching a movie at a fixed virtual image distance and, over some interval, the device subtly increases the height of screen relative to the rest of the content (e.g., by a half of a degree, 1 degree, 2, degrees, 5 degrees, etc.). The user may consciously or unconsciously adjust themselves based on the content changes. For example, if the movie is gradually moved upward over time, the user may change their posture, head angle, eye angle, and/or make other changes to their head, neck, back, eye, etc. to account for the changes. The user may move their eyes and/or neck to reorient their head orientation slightly upwards to account of the higher position of the content. Doing so may reduce fatigue, e.g., in the neck, head, and eye areas. Similarly, the yaw and/or tilt of the content may be changed to encourage user changes that also may reduce fatigue.

Changes can be configured to be subtle, e.g., unlikely to be noticed or objected to. In some implementations, the device 110 determines that virtual content has been in a static position for more than a threshold amount of time, e.g., 5 minutes, 10 minutes, 30 minutes, etc. A static device position may be associated with a static user, e.g., when a user is wearing the device. Based on this static positioning and additionally or alternatively determining that the user has been attentive to certain content during that time, the device 110 may determine to start gradually altering attributes of displayed content (e.g., virtual content or depictions of a surrounding real world environment) to inspire or encourage a user change in posture or other movement. The rate of content change (e.g., how quickly a virtual screen is shifted up over time) may be configured such that content changes are unlikely to be noticed or objected to by the user. Similarly, the amount of content change (e.g., how much a virtual screen is shifted up may be configured such that the content changes are unlikely to be noticed or object to by the user.

In some implementations, the device 110 determines to make a sequence of modifications to both be unlikely to be noticed and to collectively (e.g., after 2, 5, 10 or more relatively small changes) encourage a user change of posture or other movement. The sequence of modifications may comprise view-to-view modifications that change a parameter less than a first threshold amount between consecutive views during the presentation of the views, e.g., changes small enough from frame to frame so that they are not consciously perceptible/objectionable. The sequence of changes may comprise a cumulative modification of the parameter over the sequence of modifications that changes the parameter more than a second threshold amount, e.g., the changes being cumulatively significant enough to encourage the user to alter muscle usage to reduce fatigue or alleviate associated discomfort that might otherwise develop.

Figures 3A, 3B, 4A, 4B, 5A, 5B:
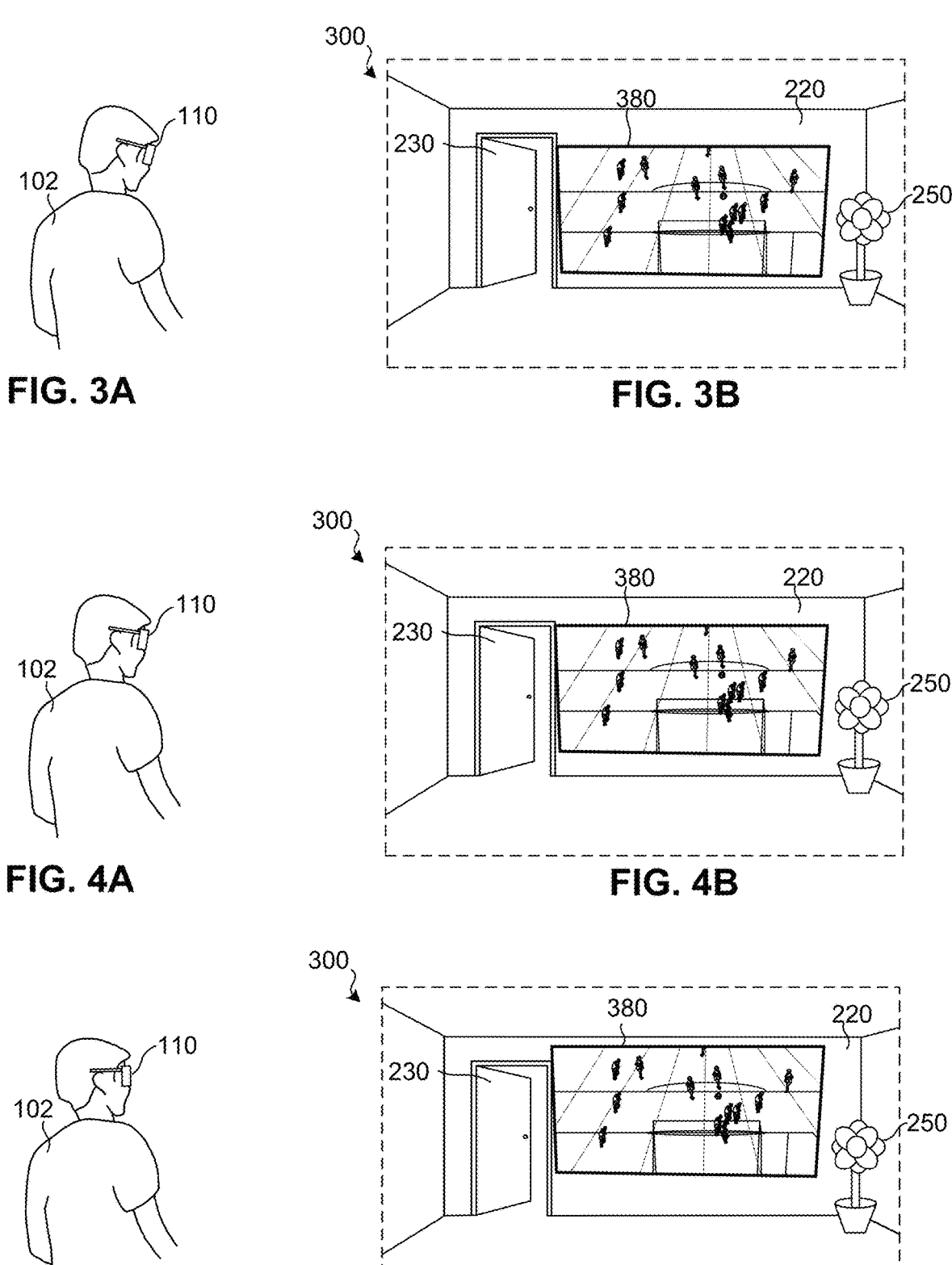
FIGS. 3A-3B illustrate an electronic device providing a view of an extended reality environment at a first point in time in accordance with some implementations.
FIGS. 4A-4B illustrate an electronic device providing a view of an extended reality environment at a second point in time in accordance with some implementations.
FIGS. 5A-5B illustrate an electronic device providing a view of an extended reality environment at a third point in time in accordance with some implementations.

FIGS. 3A-3B, 4A-4B, and 5A-5B illustrate a sequence of changes configured to both be unlikely to be noticed and to collectively encourage user change of posture or movement. In FIG. 3B, virtual content 380 is positioned relative to depictions 230, 220, 250 within the XR view 300 and the user's posture while viewing the virtual content 380 in this position is illustrated in FIG. 3A. The virtual content 380 is modified, e.g., its position in the XR view, is changed over time. Accordingly, in FIG. 4B, at a subsequent point in time the virtual content 380 has been repositioned relative to depictions 230, 220, 250 within the XR view 300 (e.g., the virtual content 380 is positioned slightly higher relative to depictions 230, 220, 250). As illustrated in FIG. 4A, the user changes body position (e.g., moving or otherwise adjusting) while viewing the virtual content 380 in this repositioned position. Similarly, in FIG. 5B, at a later subsequent point in time, the virtual content 380 has been repositioned again relative to depictions 230, 220, 250 within the XR view 300 (e.g., the virtual content 380 is further positioned to be even higher relative to depictions 230, 220, 250). As illustrated in FIG. 5A, the user changes body position (e.g., moving or otherwise adjusting) again while viewing the virtual content 380 in this further repositioned position.

In an alternative example (not shown), the user might not respond to the change between FIGS. 3B and 4B but may ultimately respond after the additional change illustrated in FIG. 5B. The change between FIGS. 3B and 4B may not be significant enough to inspire a change, but the cumulative change between FIGS. 3B and 5B may be significant enough to inspire a change. Providing the changes using intermediate steps, e.g., from the virtual content 380 position illustrated in FIG. 3B to the virtual content 380 position illustrated in FIG. 4B in a first step and then from the virtual content 380 position illustrated in FIG. 4B to the virtual content 380 position illustrated in FIG. 5B, may make the change less objectionable or noticeable than providing a change in a single step, e.g., directly moving the virtual content 380 from its position illustrated in FIG. 3B to its position illustrated in FIG. 5B. Changes may be made in small steps over time, e.g., in small steps, to reduce noticeability or objectionability.

Content changes made to encourage user body change or movement may include any number of changes, e.g., near continuous changes made every second (or even every frame) or changes made at intentionally-separated points in time, e.g., significant changes made every 10 minutes. In some implementations, the changes are configured to be subtle and unnoticeable, while in other implementations, the changes are configured to be significant and likely noticeable.

In some implementations, changes may be provided based on detecting that a user muscle fatigue condition is present. This may involve determining that the user's head, eyes, neck, etc. have remained stable or are expected to continue in a stable state based on sensor data regarding the user or information about the content, e.g., the type of content being a movie, etc. Other context information may be determined based on characteristics of the environment, the user's current state, other users in the environment, the virtual content being viewed, the user's attentive state, the time of day, the user's attributes (e.g., age, height, physical conditions, medical conditions, eye sight, etc.), typical behavior (e.g., how long a user typically works on Monday mornings, etc.) or preferences (e.g., whether a user prefers frequent, infrequent, or not fatigue-focused mitigations).

In some implementations, content changes are configured to provide content attributes that repeat or cycle over time. Such repetition or cycling over time may encourage a user to make repetitive or cyclical movements over time, e.g., encouraging a user to move their head slightly up, then slightly down, then slightly up, then slightly down, etc. In some implementations, content changes are configured to encourage a pattern of movement, e.g., encouraging the user to following a rectangular movement path of a virtual object may making corresponding movements, e.g., moving the head in a rectangular pattern over time, alternating between periods of standing up and sitting down, alternating between leaning forward and leaning back, etc.

Figure 6A:
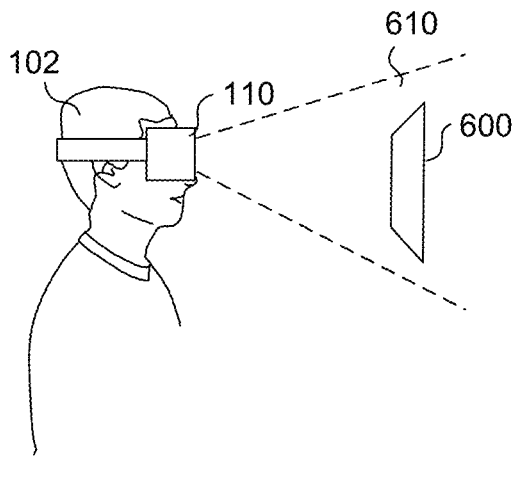
FIGS. 6A-E illustrate dynamically changing the positioning of virtual content to inspire or encourage user movement in accordance with some implementations.
Figure 6B:
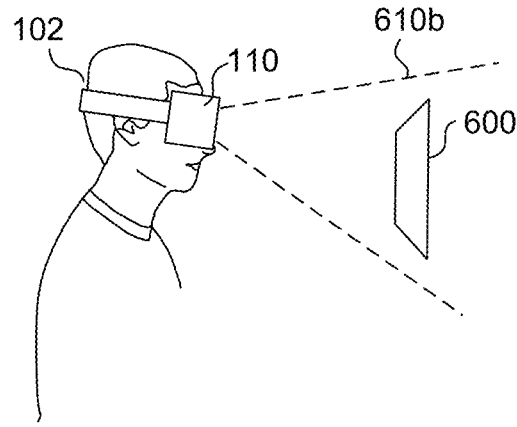
Figure 6C:
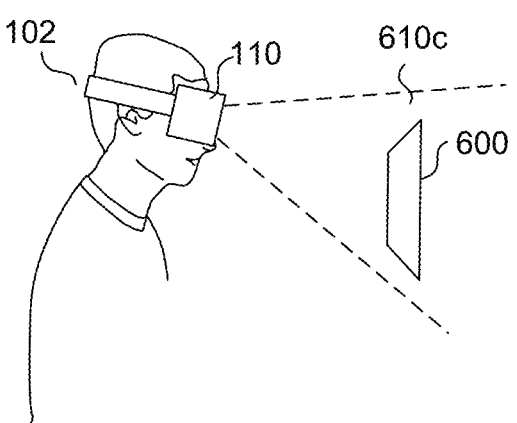
Figure 6D:
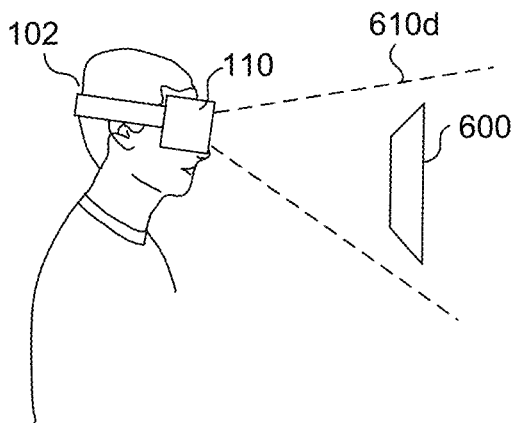
Figure 6E:
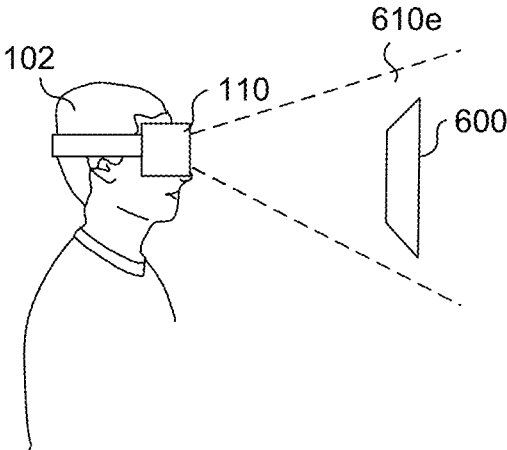

FIGS. 6A-E illustrate dynamically changing the positioning of virtual content to inspire or encourage user movement. At an initial time illustrated in FIG. 6A, the content 600 is presented at a first position and the user 102 maintains a stable head position and posture while viewing the content 600 in this position. The content 600 is then lowered to a second position, as illustrated in FIG. 6B, encouraging the user 102 to tilt their head (and/or eyes) downward slightly to view the content directly. The content 600 is then lowered further to a third position, as illustrated in FIG. 6C, encouraging the user 102 to tilt their head (and/or eyes) further downward to view the content directly. The content 600 is raised back to the second position, as illustrated in FIG. 6D, encouraging the user 102 to tilt their head (and/or eyes) upward slightly. The content 600 is then raised back to the first position, as illustrated in FIG. 6E, encouraging the user 102 to tilt their head (and/or eyes) upward slightly, returning to the initial head/eye position.

Such content movements may be repeated over time to encourage non-stable head/eye/body position over time, without requiring the user to relocate or otherwise make major body movements to continue viewing the content. In other words, the cyclical changes may enable content changes (and associated body changes) over a long period of time while the content is displayed within an acceptable viewing area (e.g., the content is displayed at variable positions within a viewing region and not displayed outside of that region, e.g., on the ceiling, floor, etc.).

In some implementations, content is repositioned and/or reoriented within a viewing area and within acceptable tilt/angle ranges. In some implementations, content pose (e.g., position and orientation) changes are made according to a predetermined path and/or process. In some implementations content pose changes are made randomly, e.g., moving the content at a rate that is below a threshold speed in directions (e.g., to make changes less noticeable/objectionable) while making those changes in way that changes the content randomly over time. Fixed pattern changes that include many variations (e.g., more than 3, 4, 5, 10, 20, etc. content positions or content positions based on variations in 2, 3, 4, 5, or 6 degrees of freedom) may encourage user posture changes or other movements that provide better fatigue and discomfort mitigation. Similarly, random changes that vary content in multiple different ways may encourage user posture changes or other movements that provide better fatigue and discomfort mitigation.

Some implementations determine to change content to encourage user movement based on determining that a user's head position, neck position, eye position, or other posture attribute has remained static (e.g., involving less than a threshold amount of movement) for a period of time (e.g., more than a threshold amount of time). For example, detecting that a user has not moved their head more than X cm (e.g., 0.1, 0.5, 1, 2, etc.) or tilted their head more than Y degrees (e.g., 0.1, 0.5, 1, 2, etc.) in the last Z time (e.g., 5 minutes, 10 minutes, 30 minutes, etc.) may trigger a content adjustment to encourage user posture changes or other movements that provide fatigue and discomfort mitigation.

A user's response to changing content may be based on automatic reorienting behavior in which a user may unconsciously change position so that their head is facing a center of a virtual object, e.g., a center of a virtual movie screen. Accordingly, in some implementations, content changes may be configured to change content such that the center of the virtual object changes position in a certain way, e.g., moving up an amount that is associated with a particular angle change of the user's head. For example, when the user is positioned relatively close to a virtual movie screen, the movie screen (e.g., its center) may be moved up an inch (or other amount) to inspire a change in user head tilt of 1 degree (or other amount) while, when the user is positioned relatively far from the virtual movie screen, the movie screen (e.g., its center) may be moved up 3 inches (or other amount) to inspire a change in user head tilt of 1 degree (or other amount).

Some implementations change virtual content to encourage a user change in focal distance. Such changes may reduce muscular eye fatigue, e.g., fatigue in the iris and the muscles in the eye that control focus. Some implementations may adjust the content to trigger an accommodation shift by the user's eyes. Some implementations utilize a varifocal display system to change focus distance and/or encourage eye changes.

In some implementations, sensors on the device 110 detect fatigue or associated discomfort, e.g., detected stress, strain, muscle tightness, muscle twitching, pain, or other user condition. For example, sensors on the device may capture images of the user's face, body, and/or eyes to monitor for face, body, or eye conditions associated with a particular user condition, capture audio to monitor sounds made by the user, and/or utilize other sensors to detect heart rate, skin temperature, eye dilation, blinking, or other user conditions. Some implementations, utilize sensor data to determine that a stress state or a strain state is present.

Some implementations determine a user posture, e.g., skeletal configuration, based on images and/or other sensor data. For example, an HMD may have downward facing sensors that capture images of the user's torso and, based on the sensor data providing device orientation data, a relative positioning (e.g., head tilt angle) may be determined.

Some implementations monitor for a head tilt that remains stable (e.g., having less than a threshold amount of movement) for more than a threshold amount of time. Some implementations identify user fatigue based on a user movement pattern, e.g., e.g., the user gradually slouching over time during an experience watching content that is displayed in a static position. Some implementations identify user micro-gestures (e.g., micro facial-expressions) and/or micro movements that are indicative of fatigue or a need for change. Some implementations utilize motion sensor data, e.g., IMU data, to determine user fatigue or associated discomfort.

In some implementations, an HMD includes internal sensors that capture images or other sensor data corresponding to the user's eyes and the areas around the user's eyes (e.g., skin wrinkles, squinting, etc.) within the eye-box of the HMD. Such eye and face information may be used to determine user condition.

In some implementations, the content that is adjusted corresponds to the physical environment around the user. For example, the device 110 may display pass-though video of a surrounding physical environment and such content may be modified to encourage user change. For example, a user may be watching a physical television device while wearing an HMD. The HMD provides passthrough of the physical environment including a depiction of the television device as well as what the television is displaying. The HMD may reposition this content (e.g., in a manner similar to moving virtual content) to encourage the user to change content. The HMD may ensure that such adjustments do not create undesirable user experiences. For example, if the depiction of the television is moved up slightly, the HMD may generate content to fill in the missing content under the television that might otherwise appear blank where a portion of the TV used to be.

Some implementations inspire or encourage user change or movement that alleviate fatigue or associated discomfort without disrupting the user, e.g., without providing a notification to the user expressly suggesting a user change. Rather, some implementations provide content changes that more subtly inspire or encourage user change in ways of which the user may not even consciously be aware.

In some implementations, content changes are constrained by various limitations. For example, virtual content may be displayed on a wall up to a ceiling and it may be undesirable to alter the content such that it appears to be in the wall or in the ceiling. Similarly, content may be displayed to appear within a defined physical boundary (e.g., a virtual movie displayed within the boundaries of a physical picture frame) and it may be undesirable to breach such boundaries with content modifications. The device 110 may account for such limitations when generating modifications to the content to inspire or encourage user change.

In some implementations, content changes may be determined (e.g., limited) based on properties of the content. For example, a virtual object that is anchored to a virtual object or a real object may be constrained with respect to movement in comparison to a virtual object that is not so anchored. There may be an expectation that anchored virtual objects maintain their positions, for example, a virtual display appearing to rest on a physical table at a particular position may be expected to remain in that position and movement of the object may be interpreted by the user as an error, e.g., a drift error made by the device's tracking system. A virtual object that is not anchored to a virtual or physical object may be more acceptable to move since changes in its position will be less apparent (e.g., movement of a 2D virtual screen floating in space may be less noticeable).

Some implementations modify content to inspire user change using modification parameters that are determined based on user reaction. For example, the device 110 may learn how much change or how quickly changes can be made before a given user starts to notice, e.g., user "A" notices screen movement of more than 0.05 degree per second while user "B" does not notice screen movements unless they exceed 0.15 degrees per second. The device 110 may modify content accordingly, e.g., in a way that each respective user is unlikely to consciously notice the changes but sufficiently that changes over time are likely to inspire user change of position or movement.

FIG. 7 is a flowchart representation of an exemplary method 700 for mitigating user fatigue or associated discomfort. In some implementations, the method 700 is performed by a device (e.g., device 110 of FIG. 1), such as a mobile device, desktop, laptop, or server device. The method 700 can be performed on a device that has a screen for displaying images and/or a screen for viewing stereoscopic images such as a head-mounted display (HMD). In some implementations, the method 700 is performed by processing logic, including hardware, firmware, software, or a combination thereof. In some implementations, the method 700 is performed by a processor executing code stored in a non-transitory computer-readable medium (e.g., a memory).

At block 702, the method 700 determines a user muscle fatigue condition associated with maintaining head, neck, or eye state stability during presentation of views via the HMD. The views comprise virtual content positioned within an XR environment. Determining (e.g., detecting) the user muscle fatigue condition may involve determining that the HMD or user's head, eyes, or neck have remained stable or are expected to continue in a stable state based on sensor data regarding the user or information about the content, e.g., the type of content being a movie, etc.

Determining the user muscle fatigue condition may comprise determining that a head, eyes, or neck of a user have remained stable for more than a threshold of time. Stability of the head, eyes, or neck may be determined based on an inertial measurement unit (IMU) of an HMD and/or using other sensor data.

Determining the user muscle fatigue condition may comprise determining that a type of the virtual content corresponds with head, eye, or neck stability. For example, virtual content that is displayed relatively consistently (e.g., a movie, TV show, or video displayed on a virtual screen that is expected to move little or none during the course of content display) may be expected to produce more head, eye, or neck stability/fatigue than virtual content having more positional variability (e.g., a virtual racecar that moves around within the environment) that is expected to produce head, eye, or neck movement over time.

Determining the user muscle fatigue condition may comprises determining a user movement pattern associated with discomfort or fatigue.

At block 704, in accordance with determining the user muscle fatigue condition, the method 700 determines a sequence of modifications to alter the views.

The sequence of modification may comprise view-to-view modifications that change a parameter less than a first threshold amount between consecutive views during the presentation of the views, e.g., changes small enough from frame to frame so that they are not consciously perceptible/objectionable.

The sequence of modification may comprise a cumulative modification of the parameter over the sequence of modifications that changes the parameter more than a second threshold amount, e.g., changes being cumulatively significant enough to encourage the user to alter muscle usage to reduce fatigue that might otherwise develop.

The cumulative modification may be configured to encourage a change in: a stable head-to-neck alignment; a stable head position; a stable head orientation; and/or a stable eye focus level.

One or more parameters may be modified in the sequence of modifications.

One or more of the parameters that are modified correspond to a vertical position of a virtual screen upon which the virtual content is displayed within the XR environment.

One or more of the parameters that are modified may correspond to a size of a virtual screen upon which the virtual content is displayed within the XR environment.

One or more of the parameters that are modified may correspond to a yaw or tilt of a virtual screen upon which the virtual content is displayed within the XR environment.

One or more of the parameters that are modified may correspond to a virtual focal distance used by the HMD to display the views.

One or more of the parameters that are modified may correspond to adjusting background content separate from the virtual content, where the background content is included as passthrough video in the views.

Modifying the one or more of the parameters may involve oscillating one or more parameters between two endpoint values over time.

In some implementations, one or more parameters are modified to encourage a change of eye focus or an accommodation shift to reduce eye fatigue. One or more of the parameters that are modified may correspond to a position of a display panel in an HMD, e.g., positioning of a varifocal display.

In some implementations, the modification of one or more parameters is determined based on detecting a user response to modification of the parameter, e.g., based on how sensitive the user is to noticing and/or unconsciously responding to a modification of a particular type or amount.

In some implementations, the one or more parameter modifications are determined based on a limitation such as a positional constraint determined based on anchoring of content within the XR environment, e.g., anchoring a movie within the boundaries of a physical picture frame on the wall.

At block 706, the method 700 presents the views in accordance with the determined sequence of modifications.

In some implementations, the virtual content depicts a movie, television series, or sporting event. In some implementations, the virtual content depicts a user interface of a productivity application (e.g., a word processor, photo editing application, etc.). In some implementations, the virtual content depicts a user interface of a social media application. In some implementations, the virtual content depicts a user interface of a game.

FIG. 8 is a block diagram of an example of the device 110 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 110 includes one or more processing units 802 (e.g., microprocessors, ASICs, FPGAs, GPUs, CPUs, processing cores, and/or the like), one or more input/output (I/O) devices and sensors 806, one or more communication interfaces 808 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, and/or the like type interface), one or more programming (e.g., I/O) interfaces 810, one or more AR/VR displays 812, one or more interior and/or exterior facing image sensor systems 814, a memory 820, and one or more communication buses 804 for interconnecting these and various other components.

In some implementations, the one or more communication buses 804 include circuitry that interconnects and controls communications between system components. In some implementations, the one or more I/O devices and sensors 806 include at least one of an inertial measurement unit (IMU), an accelerometer, a magnetometer, a gyroscope, a thermometer, an ambient light sensor (ALS), one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), and/or the like.

In some implementations, the one or more displays 812 are configured to present the experience to the user. In some implementations, the one or more displays 812 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro-mechanical system (MEMS), and/or the like display types. In some implementations, the one or more displays 812 correspond to diffractive, reflective, polarized, holographic, etc. wave-guide displays. For example, the device 110 includes a single display. In another example, the device 110 includes a display for each eye of the user.

In some implementations, the one or more image sensor systems 814 are configured to obtain image data that corresponds to at least a portion of the physical environment 100. For example, the one or more image sensor systems 814 include one or more RGB cameras (e.g., with a complimentary metal-oxide-semiconductor (CMOS) image sensor or a charge-coupled device (CCD) image sensor), monochrome cameras, IR cameras, event-based cameras, and/or the like. In various implementations, the one or more image sensor systems 814 further include illumination sources that emit light, such as a flash. In various implementations, the one or more image sensor systems 814 further include an on-camera image signal processor (ISP) configured to execute a plurality of processing operations on the image data including at least a portion of the processes and techniques described herein.

The memory 820 includes high-speed random-access memory, such as DRAM, SRAM, DDR RAM, or other random-access solid-state memory devices. In some implementations, the memory 820 includes non-volatile memory, such as one or more magnetic disk storage devices, optical disk storage devices, flash memory devices, or other non-volatile solid-state storage devices. The memory 820 optionally includes one or more storage devices remotely located from the one or more processing units 802. The memory 820 includes a non-transitory computer readable storage medium. In some implementations, the memory 820 or the non-transitory computer readable storage medium of the memory 820 stores the following programs, modules and data structures, or a subset thereof including an optional operating system 830 and one or more instruction set(s) 840.

The operating system 830 includes procedures for handling various basic system services and for performing hardware dependent tasks. In some implementations, the instruction set(s) 840 are configured to manage and coordinate one or more experiences for one or more users (e.g., a single experience for one or more users, or multiple experiences for respective groups of one or more users).

The instruction set(s) 840 include a content presentation instruction set 842 configured with instructions executable by a processor to provide content on a display of an electronic device (e.g., device 110). For example, the content may include an XR environment that includes depictions of a physical environment including real objects and virtual objects (e.g., a virtual screen overlaid on images of the real-world physical environment). The content presentation instruction set 842 is further configured with instructions executable by a processor to obtain image data (e.g., light intensity data, depth data, etc.), generate virtual data (e.g., a virtual movie screen) and integrate (e.g., fuse) the image data and virtual data (e.g., mixed reality (MR)) using one or more of the techniques disclosed herein. The content presentation instruction set 842 may provide content modifications to inspire or encourage user change or movement, as described herein.

Although these elements are shown as residing on a single device (e.g., the device 110), it should be understood that in other implementations, any combination of the elements may be located in separate computing devices. Moreover, FIG. 8 is intended more as functional description of the various features which are present in a particular implementation as opposed to a structural schematic of the implementations described herein. As recognized by those of ordinary skill in the art, items shown separately could be combined and some items could be separated. For example, some functional modules (e.g., instruction set(s) 840) shown separately in FIG. 8 could be implemented in a single module and the various functions of single functional blocks (e.g., instruction sets) could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Numerous specific details are provided herein to afford those skilled in the art a thorough understanding of the claimed subject matter. However, the claimed subject matter may be practiced without these details. In other instances, methods, apparatuses, or systems, that would be known by one of ordinary skill, have not been described in detail so as not to obscure claimed subject matter.

Implementations of the methods disclosed herein may be performed in the operation of such computing devices. The order of the blocks presented in the examples above can be varied for example, blocks can be re-ordered, combined, and/or broken into sub-blocks. Certain blocks or processes can be performed in parallel.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures. Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method, comprising:
at a head mounted device (HMD) having a processor:
   determining a user muscle fatigue condition associated with maintaining head, neck, or eye state stability during presentation of views via the HMD, the views comprising virtual content positioned within an extended reality (XR) environment;
   in accordance with determining the user muscle fatigue condition, determining a sequence of modifications to alter the views, wherein the sequence of modifications comprises:

view-to-view modifications that change a parameter less than a first threshold amount between consecutive views during the presentation of the views; and
a cumulative modification of the parameter over the sequence of modifications that changes the parameter more than a second threshold amount; and
presenting the views in accordance with the determined sequence of modifications.

2. The method of claim 1, wherein the cumulative modification is configured to encourage a change in:
   a stable head-to-neck alignment;
   a stable head position;
   a stable head orientation; or
   a stable eye focus level.

3. The method of claim 1, wherein the parameter is:
   a vertical position of a virtual screen upon which the virtual content is displayed within the XR environment;
   a size of a virtual screen upon which the virtual content is displayed within the XR environment; or
   a yaw or tilt of a virtual screen upon which the virtual content is displayed within the XR environment.

4. The method of claim 1, wherein the parameter is:
   a virtual focal distance used by the HMD to display the views, or
   a position of a display panel in the HMD.

5. The method of claim 1, wherein determining the user muscle fatigue condition comprises:
   determining that a head, eyes, or neck of a user have remained stable for more than a third threshold of time, wherein stability of the head, eyes, or neck is determined based on an inertial measurement unit (IMU) of the HMD;
   determining a type of the virtual content corresponds with head, eye, or neck stability; or
   determining a user movement pattern associated with discomfort or fatigue.

6. The method of claim 1 wherein the parameter adjusts background content separate from the virtual content, wherein the background content is included as passthrough video in the views.

7. The method of claim 1, wherein the parameter is oscillated between two endpoint values over time.

8. The method of claim 1, wherein the parameter is modified:
   to encourage an accommodation shift;
   based on detecting a user response to modification of the parameter; or
   based on a positional constraint based on anchoring of content within the XR environment.

9. A head mounted device (HMD) comprising:
   a non-transitory computer-readable storage medium; and
   one or more processors coupled to the non-transitory computer-readable storage medium, wherein the non-transitory computer-readable storage medium comprises program instructions that, when executed on the one or more processors, cause the HMD to perform operations comprising:
   determining a user muscle fatigue condition associated with maintaining head, neck, or eye state stability during presentation of views via the HMD, the views comprising virtual content positioned within an extended reality (XR) environment;
   in accordance with determining the user muscle fatigue condition, determining a sequence of modifications to alter the views, wherein the sequence of modifications comprises:

view-to-view modifications that change a parameter less than a first threshold amount between consecutive views during the presentation of the views; and a cumulative modification of the parameter over the sequence of modifications that changes the parameter more than a second threshold amount; and presenting the views in accordance with the determined sequence of modifications.

10. The HMD of claim 9, wherein the cumulative modification is configured to encourage a change in:

a stable head-to-neck alignment;

a stable head position;

a stable head orientation; or a stable eye focus level.

11. The HMD of claim 9, wherein the parameter is:

a vertical position of a virtual screen upon which the virtual content is displayed within the XR environment;

a size of a virtual screen upon which the virtual content is displayed within the XR environment; or a yaw or tilt of a virtual screen upon which the virtual content is displayed within the XR environment.

12. The HMD of claim 9, wherein the parameter is:

a virtual focal distance used by the HMD to display the views, or a position of a display panel in the HMD.

13. The HMD of claim 9, wherein determining the user muscle fatigue condition comprises:

determining that a head, eyes, or neck of a user have remained stable for more than a third threshold of time, wherein stability of the head, eyes, or neck is determined based on an inertial measurement unit (IMU) of the HMD;

determining a type of the virtual content corresponds with head, eye, or neck stability; or determining a user movement pattern associated with discomfort or fatigue.

14. The HMD of claim 9, wherein the parameter adjusts background content separate from the virtual content, wherein the background content is included as passthrough video in the views.

15. The HMD of claim 9, wherein the parameter is oscillated between two endpoint values over time.

16. The HMD of claim 9, wherein the parameter is modified:

to encourage an accommodation shift;

based on detecting a user response to modification of the parameter; or based on a positional constraint based on anchoring of content within the XR environment.

17. A non-transitory computer-readable storage medium, storing program instructions executable via a processor to perform operations comprising:

determining a user muscle fatigue condition associated with maintaining head, neck, or eye state stability during presentation of views via a head-mounted device (HMD), the views comprising virtual content positioned within an extended reality (XR) environment;

in accordance with determining the user muscle fatigue condition, determining a sequence of modifications to alter the views, wherein the sequence of modifications comprises:

view-to-view modifications that change a parameter less than a first threshold amount between consecutive views during the presentation of the views; and a cumulative modification of the parameter over the sequence of modifications that changes the parameter more than a second threshold amount; and presenting the views in accordance with the determined sequence of modifications.

18. The non-transitory computer-readable storage medium of claim 17, wherein the cumulative modification is configured to encourage a change in:

a stable head-to-neck alignment;

a stable head position;

a stable head orientation; or a stable eye focus level.

19. The non-transitory computer-readable storage medium of claim 17, wherein the parameter is:

a vertical position of a virtual screen upon which the virtual content is displayed within the XR environment;

a size of a virtual screen upon which the virtual content is displayed within the XR environment; or a yaw or tilt of a virtual screen upon which the virtual content is displayed within the XR environment.

20. The non-transitory computer-readable storage medium of claim 17, wherein the parameter is:

a virtual focal distance used by the HMD to display the views, or a position of a display panel in the HMD.

21. The non-transitory computer-readable storage medium of claim 17, wherein determining the user muscle fatigue condition comprises:

determining that a head, eyes, or neck of a user have remained stable for more than a third threshold of time, wherein stability of the head, eyes, or neck is determined based on an inertial measurement unit (IMU) of the HMD;

determining a type of the virtual content corresponds with head, eye, or neck stability; or determining a user movement pattern associated with discomfort or fatigue.

22. The non-transitory computer-readable storage medium of claim 17, wherein the parameter adjusts background content separate from the virtual content, wherein the background content is included as passthrough video in the views.

23. The non-transitory computer-readable storage medium of claim 17, wherein the parameter is oscillated between two endpoint values over time.

24. The non-transitory computer-readable storage medium of claim 17, wherein the parameter is modified:

to encourage an accommodation shift;

based on detecting a user response to modification of the parameter; or based on a positional constraint based on anchoring of content within the XR environment.

* * * * *